United States Patent
Kayano et al.

(10) Patent No.: US 10,209,387 B2
(45) Date of Patent: Feb. 19, 2019

(54) SCREENING DEVICE

(71) Applicant: Kabushiki Kaisha Toshiba, Minato-ku (JP)

(72) Inventors: Hiroyuki Kayano, Fujisawa (JP); Noritsugu Shiokawa, Yokohama (JP)

(73) Assignee: Kabushiki Kaisha Toshiba, Minato-ku (JP)

( * ) Notice: Subject to any disclaimer, the term of this patent is extended or adjusted under 35 U.S.C. 154(b) by 700 days.

(21) Appl. No.: 14/852,739

(22) Filed: Sep. 14, 2015

(65) Prior Publication Data
US 2016/0084981 A1 Mar. 24, 2016

(30) Foreign Application Priority Data
Sep. 19, 2014 (JP) .................................. 2014-191785

(51) Int. Cl.
| | | |
|---|---|---|
| A61B 5/05 | (2006.01) |
| G01N 21/00 | (2006.01) |
| G01V 3/12 | (2006.01) |
| G01V 3/38 | (2006.01) |
| G01V 8/00 | (2006.01) |
| G01S 13/88 | (2006.01) |

(52) U.S. Cl.
CPC .............. *G01V 3/12* (2013.01); *G01S 13/887* (2013.01); *G01V 3/38* (2013.01); *G01V 8/005* (2013.01); *A61B 5/0507* (2013.01); *G01N 21/00* (2013.01)

(58) Field of Classification Search
CPC ...... G01S 13/88; G01S 13/887; G01S 13/888; A61B 5/05; A61B 5/0507; A61B 5/053; A61B 5/103; A61B 5/107; A61B 5/1075; G01N 21/00
See application file for complete search history.

(56) References Cited

U.S. PATENT DOCUMENTS 3,713,156 A * 1/1973 Pothier ..................... G01S 7/04
342/179
4,135,131 A * 1/1979 Larsen ................. A61B 5/0002
324/615

(Continued)

FOREIGN PATENT DOCUMENTS

| JP | 5-102904 A | 4/1993 |
| JP | 2000-275289 A | 10/2000 |

(Continued)

OTHER PUBLICATIONS

Extended European Search Report dated May 3, 2016 in Patent Application No. 15184748.0.
(Continued)

*Primary Examiner* — Peter M Bythrow
(74) *Attorney, Agent, or Firm* — Oblon, McClelland, Maier & Neustadt, L.L.P.

(57) ABSTRACT

According to one embodiment, a screening device includes a first antenna configured to transmit a first microwave to a subject to generate a second microwave and a third microwave, the second microwave being generated by a diffraction of the first microwave at the subject, the third microwave being a part of the first microwave passing the subject, and a second antenna configured to receive the second microwave in a first period and to receive the third microwave in a second period.

17 Claims, 9 Drawing Sheets

(56) References Cited

U.S. PATENT DOCUMENTS

| | | | | |
|---|---|---|---|---|
| 4,641,659 A * | 2/1987 | Sepponen | A61B 5/05 | |
| | | | 600/430 | |
| 4,774,961 A * | 10/1988 | Carr | A61B 5/015 | |
| | | | 374/E11.003 | |
| 4,975,968 A * | 12/1990 | Yukl | G01N 22/00 | |
| | | | 324/647 | |
| 5,073,782 A * | 12/1991 | Huguenin | G01S 7/024 | |
| | | | 250/332 | |
| 5,265,144 A * | 11/1993 | Harding | A61B 6/032 | |
| | | | 378/147 | |
| 5,361,070 A * | 11/1994 | McEwan | A61B 5/0507 | |
| | | | 342/21 | |
| 5,455,590 A * | 10/1995 | Collins | G01S 13/887 | |
| | | | 342/179 | |
| 5,573,012 A * | 11/1996 | McEwan | A61B 5/024 | |
| | | | 600/428 | |
| 5,661,494 A * | 8/1997 | Bondyopadhyay | H01Q 1/364 | |
| | | | 343/700 MS | |
| 5,829,437 A * | 11/1998 | Bridges | A61B 5/05 | |
| | | | 600/430 | |
| 5,844,407 A * | 12/1998 | Hubbell | G01R 33/0354 | |
| | | | 324/72 | |
| 6,057,761 A * | 5/2000 | Yukl | A61B 5/0507 | |
| | | | 250/358.1 | |
| 6,292,143 B1 * | 9/2001 | Romanofsky | H01Q 1/38 | |
| | | | 343/700 MS | |
| 6,359,582 B1 * | 3/2002 | MacAleese | G01S 7/417 | |
| | | | 342/192 | |
| 6,363,268 B1 * | 3/2002 | Schuchardt | H01Q 1/364 | |
| | | | 342/368 | |
| 6,480,141 B1 * | 11/2002 | Toth | G01N 22/00 | |
| | | | 324/639 | |
| 6,777,684 B1 * | 8/2004 | Volkov | G01N 21/3581 | |
| | | | 250/341.1 | |
| 6,876,322 B2 * | 4/2005 | Keller | G01N 21/3581 | |
| | | | 342/179 | |
| 6,927,691 B2 * | 8/2005 | Yukl | G01S 13/887 | |
| | | | 340/540 | |
| 6,937,182 B2 * | 8/2005 | Lovberg | G01S 13/887 | |
| | | | 342/179 | |
| 6,967,612 B1 * | 11/2005 | Gorman | G01S 7/024 | |
| | | | 342/175 | |
| 7,013,245 B2 * | 3/2006 | Kotter | G06K 9/00771 | |
| | | | 702/189 | |
| 7,043,271 B1 | 5/2006 | Seto et al. | | |
| 7,119,740 B2 * | 10/2006 | Blasing | G01S 13/887 | |
| | | | 342/179 | |
| 7,183,963 B2 * | 2/2007 | Lee | G01N 22/00 | |
| | | | 342/175 | |
| 7,194,236 B2 * | 3/2007 | Lovberg | G01S 13/887 | |
| | | | 250/252.1 | |
| 7,212,153 B2 * | 5/2007 | Rowe | G01S 13/887 | |
| | | | 342/179 | |
| 7,230,564 B2 * | 6/2007 | Basir | G01N 22/00 | |
| | | | 342/175 | |
| 7,253,766 B2 * | 8/2007 | Foote | G01S 13/003 | |
| | | | 342/179 | |
| 7,295,146 B2 * | 11/2007 | McMakin | G01S 7/026 | |
| | | | 342/179 | |
| 7,365,672 B2 * | 4/2008 | Keller | G01N 21/3581 | |
| | | | 342/179 | |
| 7,405,692 B2 * | 7/2008 | McMakin | G01S 7/20 | |
| | | | 342/22 | |
| 7,415,244 B2 * | 8/2008 | Kolinko | G01V 8/005 | |
| | | | 342/179 | |
| 7,417,440 B2 * | 8/2008 | Peschmann | G01V 5/0016 | |
| | | | 250/250 | |
| 7,492,303 B1 * | 2/2009 | Levitan | G01S 7/024 | |
| | | | 342/188 | |
| 7,791,355 B1 * | 9/2010 | Esher | G01R 29/0871 | |
| | | | 324/637 | |
| 7,804,442 B2 * | 9/2010 | Ammar | G01S 17/89 | |
| | | | 342/179 | |
| 7,809,427 B2 * | 10/2010 | Winters | A61B 5/05 | |
| | | | 382/131 | |
| 7,844,081 B2 * | 11/2010 | McMakin | G01S 13/887 | |
| | | | 382/115 | |
| 7,889,113 B2 * | 2/2011 | Cardiasmenos | G01N 21/3581 | |
| | | | 342/175 | |
| 7,920,088 B2 * | 4/2011 | Thompson | G01S 7/414 | |
| | | | 342/118 | |
| 8,207,893 B2 * | 6/2012 | Baliarda | H01Q 1/36 | |
| | | | 343/700 MS | |
| 8,390,504 B2 * | 3/2013 | Abdillah | G01S 7/412 | |
| | | | 342/22 | |
| 8,674,875 B2 * | 3/2014 | Carter | G01S 13/003 | |
| | | | 342/118 | |
| 8,736,486 B2 * | 5/2014 | Stolpman | A61B 5/0507 | |
| | | | 342/165 | |
| 8,946,641 B2 * | 2/2015 | Smith | G01S 7/412 | |
| | | | 250/338.1 | |
| 9,229,102 B1 * | 1/2016 | Wright | G01S 13/888 | |
| 9,332,922 B2 * | 5/2016 | Persson | A61B 5/05 | |
| 9,572,511 B2 * | 2/2017 | Kochba | A61B 5/0507 | |
| 2002/0140615 A1 * | 10/2002 | Carles | H01Q 1/36 | |
| | | | 343/725 | |
| 2004/0080315 A1 * | 4/2004 | Beevor | G01V 3/104 | |
| | | | 324/244 | |
| 2004/0239337 A1 * | 12/2004 | Jean | G01N 22/00 | |
| | | | 324/638 | |
| 2005/0093733 A1 * | 5/2005 | Lovberg | G01V 8/005 | |
| | | | 342/22 | |
| 2005/0107693 A1 * | 5/2005 | Fear | A61B 5/05 | |
| | | | 600/430 | |
| 2005/0110672 A1 * | 5/2005 | Cardiasmenos | G01N 21/3581 | |
| | | | 342/27 | |
| 2005/0232459 A1 * | 10/2005 | Rowe | G01S 13/86 | |
| | | | 382/100 | |
| 2005/0285772 A1 * | 12/2005 | Basir | G01N 22/00 | |
| | | | 342/22 | |
| 2006/0017605 A1 * | 1/2006 | Lovberg | G01K 7/226 | |
| | | | 342/22 | |
| 2006/0109160 A1 | 5/2006 | Baharav et al. | | |
| 2006/0109174 A1 * | 5/2006 | Baharav | G01S 13/04 | |
| | | | 342/179 | |
| 2006/0214835 A1 * | 9/2006 | Lee | G01N 22/00 | |
| | | | 342/22 | |
| 2007/0114418 A1 * | 5/2007 | Mueller | G01J 3/42 | |
| | | | 250/341.1 | |
| 2007/0158571 A1 * | 7/2007 | Cole | G01N 21/3581 | |
| | | | 250/341.8 | |
| 2008/0043102 A1 | 2/2008 | Rowe et al. | | |
| 2008/0119363 A1 * | 5/2008 | Bernstein | H01F 21/00 | |
| | | | 505/211 | |
| 2009/0073023 A1 * | 3/2009 | Ammar | G01S 13/887 | |
| | | | 342/22 | |
| 2009/0271146 A1 * | 10/2009 | Ammar | G01S 7/411 | |
| | | | 702/155 | |
| 2009/0322873 A1 * | 12/2009 | Reilly | G01S 7/411 | |
| | | | 348/143 | |
| 2010/0278401 A1 * | 11/2010 | Schoenbach | A61B 5/05 | |
| | | | 382/128 | |
| 2010/0295725 A1 * | 11/2010 | Krozer | G01S 13/003 | |
| | | | 342/25 A | |
| 2011/0050480 A1 * | 3/2011 | Kroning | G01S 7/025 | |
| | | | 342/27 | |
| 2011/0080315 A1 * | 4/2011 | Reilly | G01S 13/86 | |
| | | | 342/175 | |
| 2012/0105267 A1 * | 5/2012 | DeLia | G01S 13/86 | |
| | | | 342/22 | |
| 2012/0262328 A1 * | 10/2012 | Shinonaga | H01Q 3/36 | |
| | | | 342/27 | |
| 2013/0022237 A1 * | 1/2013 | Kuznetsov | G01S 13/867 | |
| | | | 382/103 | |

(56) References Cited

U.S. PATENT DOCUMENTS

2014/0010124 A1* 1/2014 Kumamoto ............... H04L 5/18
370/278
2015/0084645 A1 3/2015 Kayano et al.
2016/0143558 A1* 5/2016 Chernokalov ....... A61B 5/0507
600/430

FOREIGN PATENT DOCUMENTS

| JP | 2001-86058 A | 3/2001 |
|----|--------------|--------|
| JP | 2005-501262 A | 1/2005 |
| JP | 2006-145541 | 6/2006 |
| JP | 2007-536506 A | 12/2007 |
| JP | 2009-125257 | 6/2009 |
| JP | 2009-125457 | 6/2009 |
| JP | 2010-204055 | 9/2010 |
| JP | 2015-87378 A | 5/2015 |

OTHER PUBLICATIONS

Jeffery T. Williams, et al., "High Temperature Superconductors and Their Application in Passive Antenna Systems" IEEE Antennas and propagation Magazine, vol. 32, No. 4, XP011419788, Aug. 1990, pp. 7-18.

Kunihko Mabuchi, "Advanced Techniques and Clinical Applications in Biomedical Thermology" URL:https://books.google.nl/books?id=czdRMwEACAAJ&dq=advanced+techniques+clinical+application+biomedical+thermaology&hl=de&sa=X&redir_esc=y, XP055265457, Jan. 1, 1995, pp. 64-65.

* cited by examiner

SCREENING DEVICE

CROSS-REFERENCE TO RELATED APPLICATIONS

This application is based upon and claims the benefit of priority from the prior Japanese Patent Application No. 2014-191785, filed on Sep. 19, 2014; the entire contents of which are incorporated herein by reference.

FIELD

Embodiments described herein relate to a screening device.

BACKGROUND

Currently, a general security system used in airports and the like uses X-rays to verify articles possessed by a screening subject. However, even though the X-rays pass through the body for only a short period of time, the screening subject is undesirably exposed to radiation by the X-rays. In the case where screening is performed using a metal detector, it is possible to verify metal objects; but only relatively large objects can be verified; and unfortunately, objects possessed inside the body and substances other than metals cannot be identified. In a relatively new method to be utilized, substances other than metals can be verified by using terahertz waves. In such a method, clothing and the like can be penetrated; but verification of the interior of the body cannot be performed; and problems concerning privacy arise because body lines due to reflections at the body surface are viewed as-is.

DETAILED DESCRIPTION

According to one embodiment, a screening device includes a first antenna configured to transmit a first microwave to a subject to generate a second microwave and a third microwave, the second microwave being generated by a diffraction of the first microwave at the subject, the third microwave being a part of the first microwave passing the subject, and a second antenna configured to receive the second microwave in a first period and to receive the third microwave in a second period.

Embodiments of the invention will now be described with reference to the drawings.

First, a first embodiment will be described.

Figure 1:
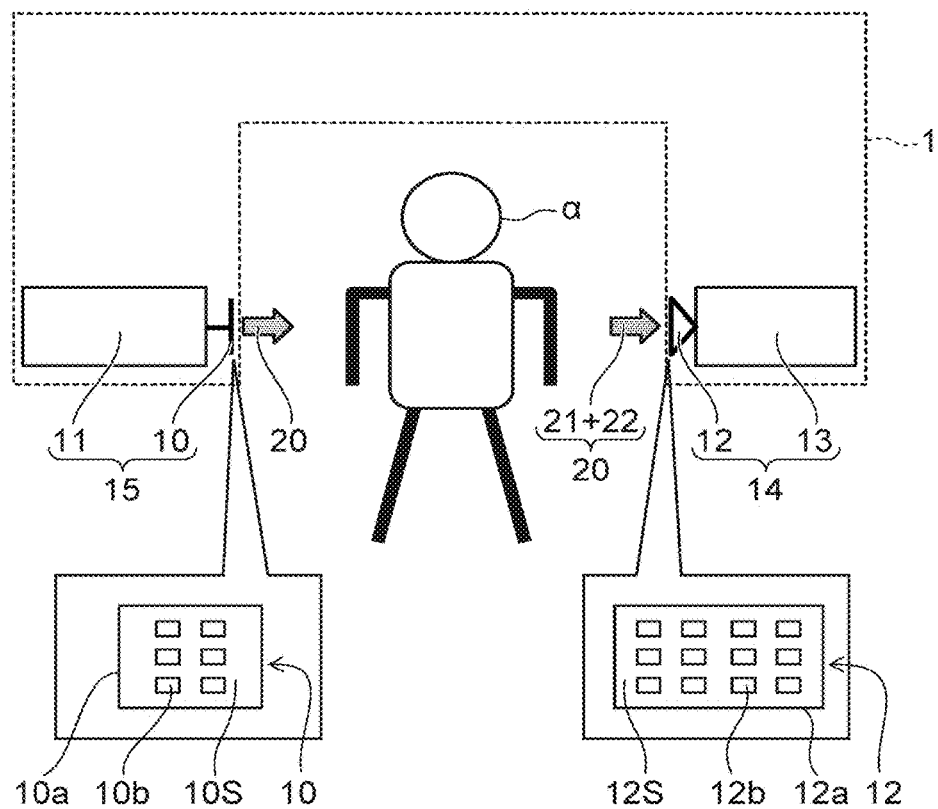
FIG. 1 is a conceptual view showing a screening device according to a first embodiment.

FIG. 1 is a conceptual view showing a screening device according to the first embodiment.

As shown in FIG. 1, a transmitting antenna unit 15 (first antenna) that includes a transmitter 11 and a transmitting antenna 10 is provided in the screening device 1 according to the embodiment, where the transmitter 11 transmits a microwave having a pulse form, i.e., a pulse microwave 20 (first microwave). A receiving antenna unit 14 (second antenna) that includes a directional antenna 12 and a receiver 13 is further provided.

A dielectric plate 10a is provided in the transmitting antenna 10. The dielectric plate 10a has a first surface 10S. A plurality of elements 10b are provided on the first surface 10S in transmitting antenna 10. A dielectric plate 12a is provided in the directional antenna 12. The dielectric plate 12b has a second surface 12S. A plurality of elements 12b are provided on the surface 12S in directional antenna 12.

The number of elements 12b of the directional antenna is greater than the number of elements 10b of the transmitting antenna 10. Generally, the directivity of the antenna increases proportionally to the number of the elements that are included in the antenna. The first surface 10S of the transmitting antenna 10 and the second surface 12S of the directional antenna 12 are disposed to face each other, for example. A screening subject α is disposed between the transmitting antenna 10 and the directional antenna 12 when screening. The screening subject α is, for example, a passenger of an airplane.

As the directional antenna 12, it is favorable to use an antenna having high directivity such as a superconducting antenna made of a superconducting material, etc. The superconducting antenna includes a superconductor film including at least one type of element of yttrium (Y), barium (Ba), copper (Cu), lanthanum (La), tantalum (Ta), bismuth (Bi), strontium (Sr), calcium (Ca), lead (Pb), or the like patterned into the desired antenna pattern configuration. For example, known patterning technology such as lithography or the like is used for the patterning. For example, the superconducting antenna may be patterned into a pattern configuration such as monopole, dipole, crank-shaped, spiral having a rectangular, circular, elliptical, or other shape, L-shaped, reverse F-shaped, etc. A coplanar waveguide-type antenna in which the ground and signal planes are in the same plane and that has a length that is an integer multiple of the quarter wavelength may be used; or a slot antenna may be used in which a slot is provided in a portion of the ground.

As the directional antenna 12, it is more favorable to use an array antenna in which a superconducting antenna and a power supply path are provided on a low loss dielectric substrate and a planar antenna including the ground pattern is stacked. It is more favorable to use an end-fire array antenna or a broadside array antenna as the array antenna.

Operations of the screening device 1 according to the embodiment will now be described.

Figure 2A:
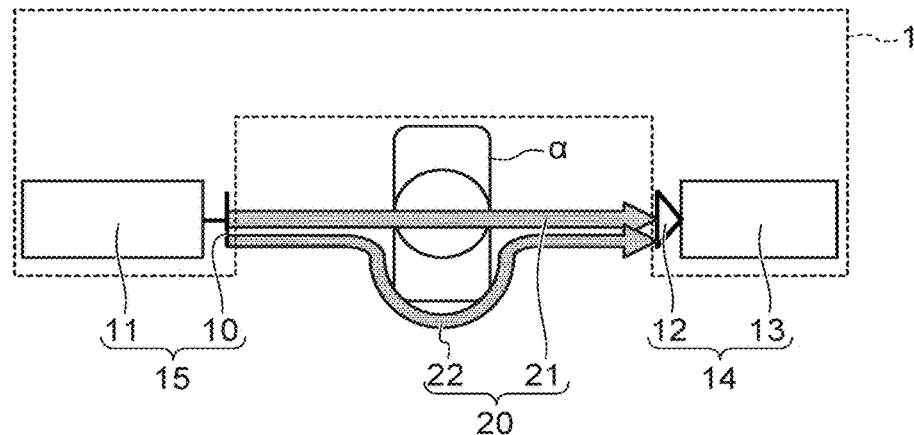
FIG. 2A is a conceptual view showing the screening device according to the first embodiment.
Figure 2B:
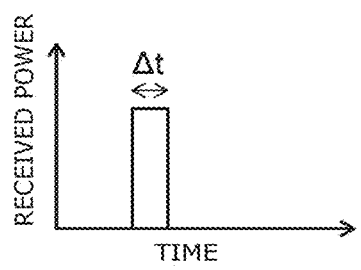
FIG. 2B is a graph of a irradiation profile of a pulse microwave.
Figure 2C:
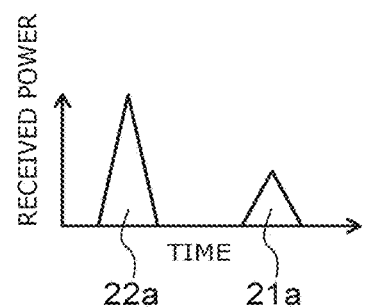
FIG. 2C is a graph of a reception profile of a diffracted wave and a transmitted wave.

FIG. 2A is a conceptual view showing the screening device according to the embodiment; FIG. 2B is a graph of the irradiation profile of the pulse microwave, where the horizontal axis is time, and the vertical axis is the intensity of the pulse microwave; and FIG. 2C is a graph of the reception profile of the diffracted wave and the transmitted wave, where the horizontal axis is time, and the vertical axis is the received power.

In the screening device 1 according to the embodiment, the screening is performed by disposing the screening subject α between the transmitting antenna 10 and the directional antenna 12 as shown in FIG. 2A. The pulse microwave 20 is irradiated toward the screening subject α from the transmitting antenna unit 15 after activating the receiving antenna unit 14. Thereby, a diffracted wave 22 (second microwave) and a transmitted wave 21 (third microwave) are incident on the directional antenna 12 and are received by the receiver 13. The transmitted wave 21 is the pulse microwave 20 that passes through the screening subject α; and the diffracted wave 22 is the pulse microwave 20 that is diffracted by the screening subject α.

As shown in FIG. 2B, the pulse microwave 20 that is transmitted from the transmitting antenna unit 15 is irradiated only for a short period of time (Δt). The pulse microwave 20 that is irradiated is divided into the transmitted wave 21 that passes through the screening subject α and the diffracted wave 22 that is diffracted by the screening subject α. At this time, a difference occurs between the travel speeds of the transmitted wave 21 and the diffracted wave 22 due to the difference between the relative dielectric constant of the screening subject α and the relative dielectric constant in air.

The velocity of the pulse microwave 20 is expressed by Formula 1 recited below, where the velocity of the pulse microwave 20 is v, the speed of light is c, and the relative dielectric constant of the substance through which the pulse microwave 20 passes through is Er.

$$v=c/\sqrt{(Er)} \quad \text{[Formula 1]}$$

In other words, the travel speed of the pulse microwave 20 decreases as the value of the relative dielectric constant increases for the substance through which the pulse microwave 20 passes. Accordingly, in the case where the transmitted wave 21 passes through the screening subject α, e.g., a human body, etc., having a relative dielectric constant greater than the relative dielectric constant in air, the travel speed of the transmitted wave 21 is slower than the travel speed of the diffracted wave 22.

As shown in FIG. 2C, the receiver 13 can detect the microwave signal received by the directional antenna 12 as being temporally separated into a signal 21a of the transmitted wave 21 and a signal 22a of the diffracted wave 22.

In other words, the receiving antenna unit 14 receives the diffracted wave 22 in a first period. And the receiving antenna unit 14 receives the transmitted wave 21 in a second period. The receiving antenna unit 14 does not receive the transmitted wave 21 in the second period. And the receiving antenna unit 14 does not receive the third microwave in the first time.

Then, an image of the screening subject α can be made by performing the prescribed processing of the signals and by integrating the results. The image shows the existence, configuration, etc., of an object made of a metal or a dielectric possessed by the screening subject α inside the body or outside the body.

The irradiation time (Δt) of the pulse microwave 20 is such that the transmitted wave 21 and the diffracted wave 22 received by the directional antenna 12 can be detected separately as the signal 21a and the signal 22a by the receiver 13. Also, the frequency band and intensity of the pulse microwave 20 are such that the pulse microwave 20 can pass through the screening subject α, and the transmitted wave 21 and the diffracted wave 22 can be separated into the signals 21a and 22a when detected by the receiver 13.

Figure 3:
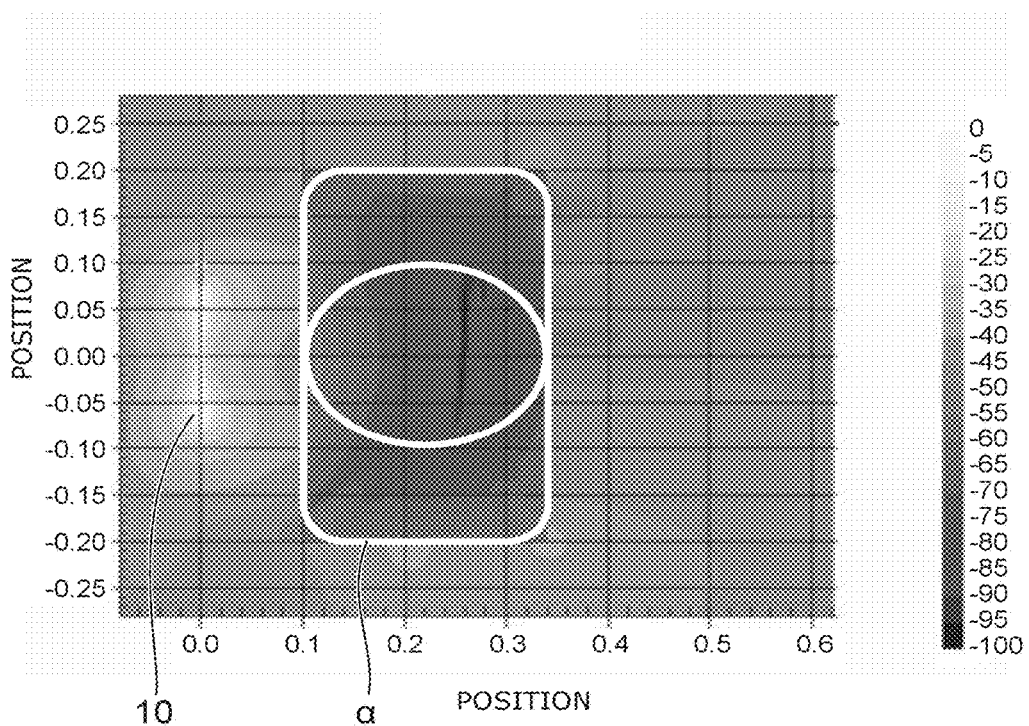
FIG. 3 is a graph of a state of an electric field when a pulse microwave is irradiated toward a screening subject according to the first embodiment.

FIG. 3 is a graph of the state of the electric field when a pulse microwave is irradiated toward the screening subject from the transmitting antenna unit of the screening device according to the embodiment. In the graph of FIG. 3, darker shading illustrates a lower electric field strength.

As shown in FIG. 3, it is confirmed that an electric field also is generated at the rear of the screening subject α when the pulse microwave 20 is irradiated on the screening subject α. Accordingly, it can be said that the pulse microwave 20 that is irradiated from the transmitting antenna 10 toward the screening subject α is diffracted rearward of the screening subject α.

Effects of the embodiment will now be described.

In the embodiment, for example, in the case where the screening subject α is a human body, it is possible to perform the screening of the screening subject α using microwaves without exposing the human body to electromagnetic waves in the short wavelength band such as X-rays, etc., that may have negative effects on organisms. Also, because the screening subject α has a relative dielectric constant that is different from the relative dielectric constant of air, a difference occurs between the travel speeds of the transmitted wave 21 passing through the screening subject α and the diffracted wave 22 diffracted by the screening subject α. For example, in the case where the screening subject α is a human body, the relative dielectric constant in air is 1; the relative dielectric constant of the human body is about 170; and therefore, when performing the measurement in air, compared to the diffracted wave 22, the travel speed of the transmitted wave 21 is about 13 ($\sqrt{170}$) times slower.

In the embodiment, by irradiating the microwave in a pulse form, it is possible for the receiving antenna unit 14 to separately detect the transmitted wave 21 passing through the screening subject α and the diffracted wave 22 diffracted by the screening subject α. Thereby, it is possible to screen the interior of the screening subject α by detecting the transmitted wave 21 and to screen the surface of the screening subject α by detecting the diffracted wave 22.

For example, in the case where the screening subject α has a metal or the like inside its body, the pulse microwave 20 is reflected at the portion where the metal exists; and the pulse microwave 20 passes through the other portions. Accordingly, it is possible to perform metal detection of the interior of the screening subject α by detecting the transmitted wave 21 which is the pulse microwave 20 passing through the screening subject α.

According to the embodiment, it is possible to screen the interior of the screening subject α without exposing the screening subject α to electromagnetic waves in the short wavelength band which may have negative effects on organisms. Also, the body surface can be screened using the diffracted wave 22 while performing the screening of the interior of the screening subject α using the transmitted wave 21. Also, the physique of the screening subject α can be roughly estimated from the time for the diffracted wave 22 to reach the directional antenna 12.

A second embodiment will now be described.

Figure 4:
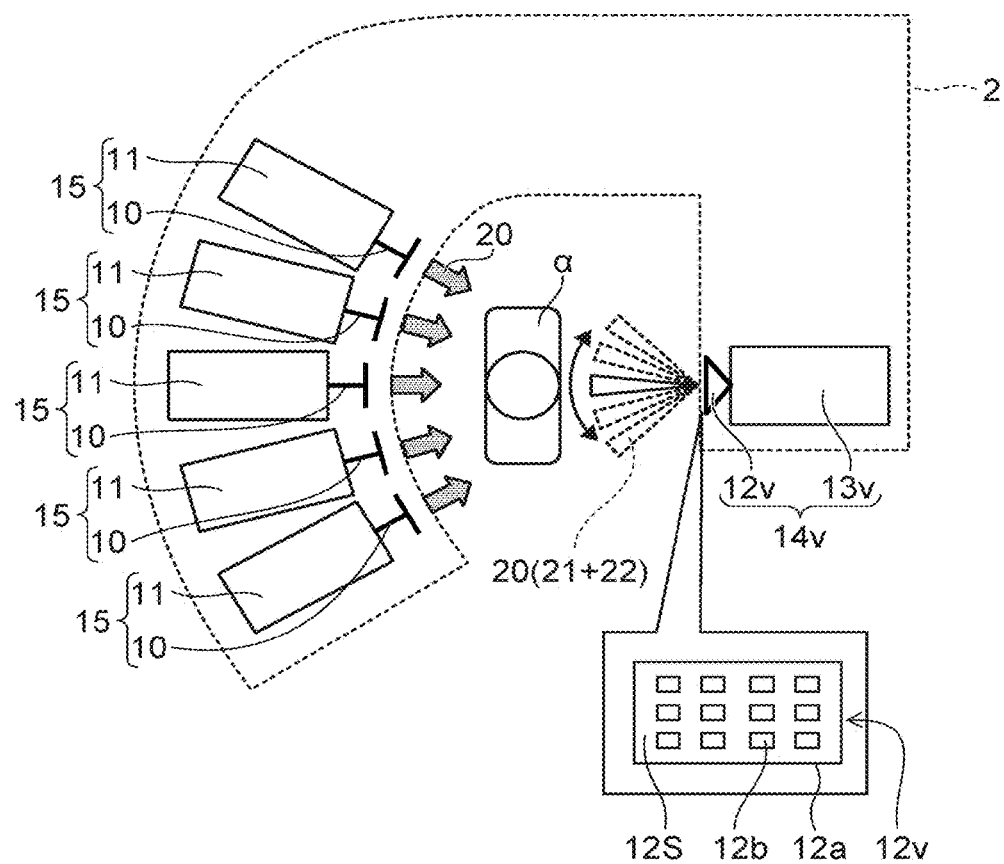
FIG. 4 is a conceptual view showing a screening device according to a second embodiment.

FIG. 4 is a conceptual view showing a screening device according to the embodiment.

As shown in FIG. 4, the screening device 2 according to the embodiment includes, for example, a variable receiving antenna unit 14v that includes a receiver 13v and a variable directional antenna 12v that can receive the pulse microwaves 20 from multiple directions by including multiple receiving elements and by providing the detection signals for the receiving elements with a prescribed phase difference. A dielectric plate 12a is provided in the variable directional antenna 12v. The dielectric plate 12b has a second surface 12S. A plurality of elements 12b are provided on the second surface 12S in variable directional antenna 12v. The number of elements 12b of the variable directional antenna 12v is greater than the number of elements 10b of the transmitting antenna 10. The variable receiving antenna unit 14v can be moved in the vertical direction. Multiple transmitting antennas 10 are disposed on a circular arc having the variable directional antenna 12v at the center.

The screening subject α is disposed between the variable directional antenna 12v and the transmitting antennas 10 when screening the screening subject α.

Effects of the embodiment will now be described.

When the pulse microwaves 20 from the multiple transmitting antenna units 15 are irradiated on the screening subject α, the variable receiving antenna unit 14v receives the diffracted waves 22 and the transmitted waves 21 passing through the screening subject.

By using the variable directional antenna 12v, the receiver can detect the signals of the pulse microwaves transmitted from the multiple transmitting antenna units 15. In such a case, the precision of the screening information can be increased by increasing the directivity of the variable directional antenna 12v. Also, by moving the variable receiving antenna unit 14v in the vertical direction, the pulse microwaves 20 can be used to scan the screening subject α in the vertical direction. Thereby, the screening information can be acquired for a wider area of the screening subject α.

According to the embodiment, by using the variable receiving antenna unit 14v and the multiple transmitting antenna units 15, the entire screening subject α or any portion of the screening subject α can be scanned using a beam having narrow directivity. Thereby, the screening information can be acquired for a wider area of the screening subject α.

A third embodiment will now be described.

Figure 5:
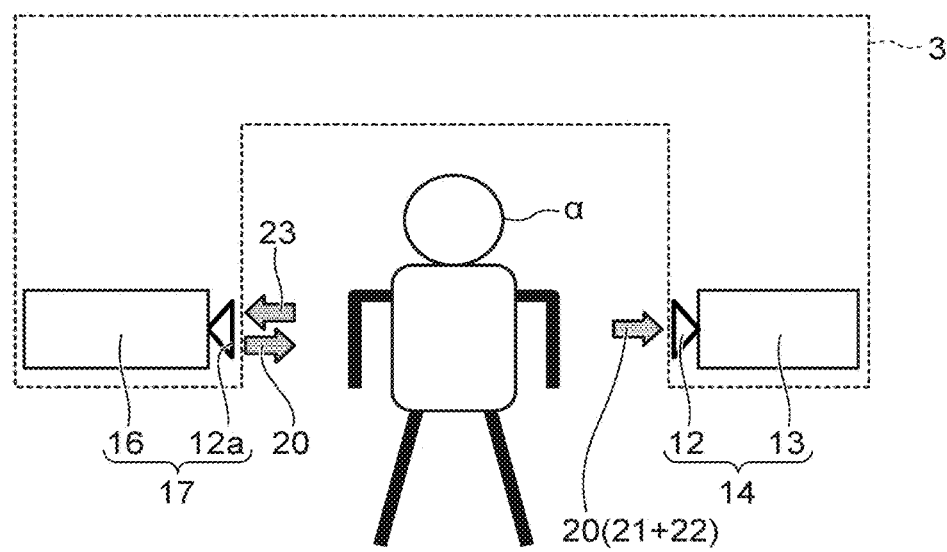
FIG. 5 is a conceptual view showing a screening device according to a third embodiment.

FIG. 5 is a conceptual view showing a screening device according to the embodiment.

As shown in FIG. 5, the screening device 3 according to the embodiment differs from the screening device according to the first embodiment described above (referring to FIG. 1) in that a transmitting/receiving antenna unit 17 is provided instead of the transmitting antenna unit 15. A transmitter/receiver 16 that can both transmit and receive the pulse microwave 20 is provided in the transmitting/receiving antenna unit 17; and a directional antenna 12a which is a first directional antenna that can receive a reflected wave 23 is connected to the transmitter/receiver 16. The directional antenna 12 (a second directional antenna) of the receiving antenna unit 14 is provided to oppose the directional antenna 12a.

Operations of the screening device 3 according to the embodiment will now be described.

Figure 6A:
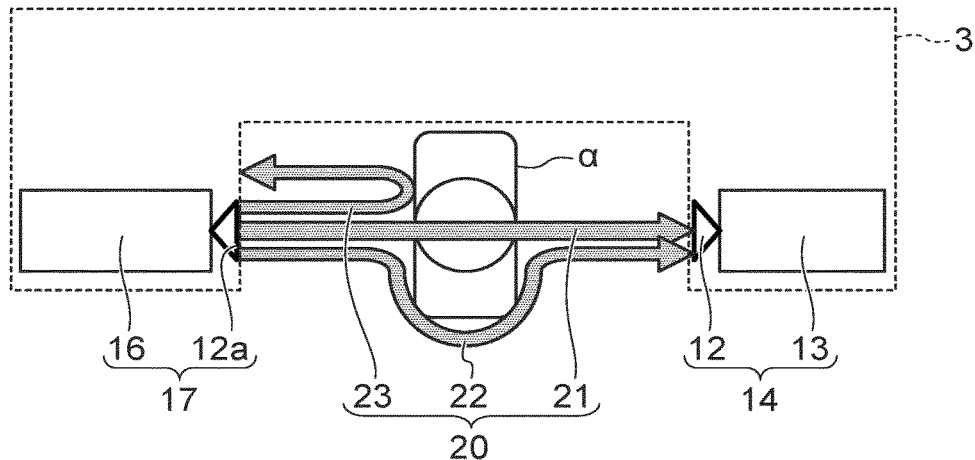
FIG. 6A is a conceptual view showing the screening device according to the third embodiment.
Figure 6B:
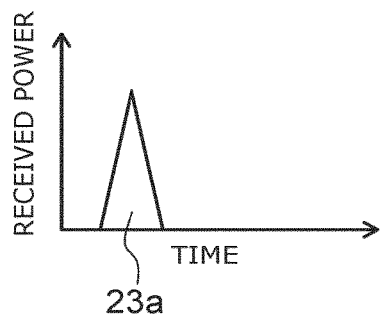
FIG. 6B is a graph of a reception profile of a reflected wave.

FIG. 6A is a conceptual view showing the screening device according to the embodiment; FIG. 6B is a graph of the reception profile of the reflected wave, where the horizontal axis is time, and the vertical axis is the received power; and FIG. 6C is a graph of the reception profile of the diffracted wave and the transmitted wave, where the horizontal axis is time, and the vertical axis is the received power.

In the embodiment as shown in FIG. 6A, the pulse microwave 20 is irradiated from the transmitting/receiving antenna unit 17 toward the screening subject α. The pulse microwave 20 that is irradiated is divided into the transmitted wave 21 that passes through the screening subject α, the diffracted wave 22 that is diffracted by the screening subject α, and the reflected wave 23 that is reflected by the screening subject α.

Similarly to the first embodiment, the transmitted wave 21 and the diffracted wave 22 are received by the receiving antenna unit 14. The reflected wave 23 is received by the transmitting/receiving antenna unit 17.

Figure 6C:
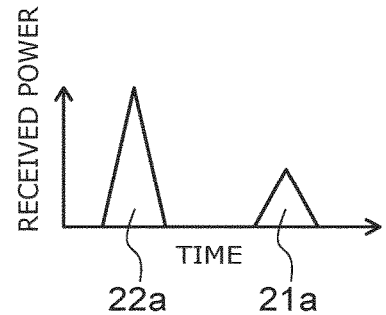
FIG. 6C is a graph of a reception profile of a diffracted wave and a transmitted wave.

As shown in FIGS. 6B and 6C, the reflected wave 23 that is received by the directional antenna 12a is detected by the transmitter/receiver 16 as a signal 23a. Similarly to the first embodiment, the transmitted wave 21 and the diffracted wave 22 are detected by the receiving antenna unit 14 as the signals 21a and 22a which are temporally separated.

Effects of the embodiment will now be described.

In the embodiment, the screening of the interior of the screening subject α can be performed by detecting the transmitted wave 21; and the screening of the surface of the screening subject α can be performed by detecting the diffracted wave 22. In addition to the screening of the surface of the screening subject α by detecting the reflected wave 23, the transmitting/receiving antenna unit 17 also can acquire positional information. It is possible to obtain precise positional information of the screening subject α from the screening information obtained by detecting the reflected wave 23; and the precision of the screening can be increased by combining the screening information obtained by receiving the diffracted wave 22 and the screening information obtained by receiving the reflected wave 23.

According to the embodiment, the screening information can be obtained with higher precision by the transmitting/receiving antenna unit 17 and the receiving antenna unit 14 receiving the transmitted wave 21, the diffracted wave 22, and the reflected wave 23.

A fourth embodiment will now be described.

Figure 7:
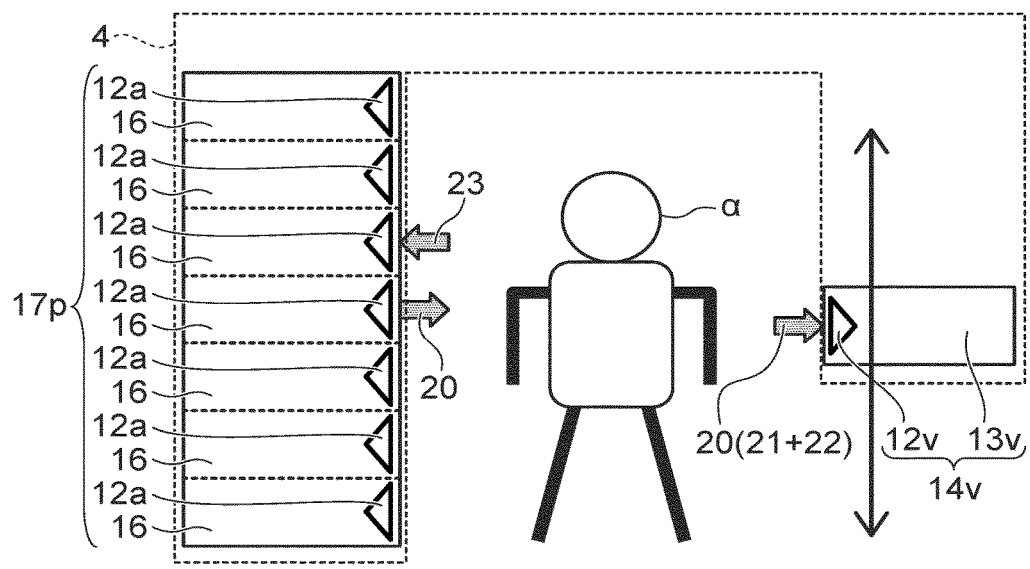
FIG. 7 is a conceptual view showing a screening device according to a fourth embodiment.

FIG. 7 is a conceptual view showing a screening device according to the embodiment.

As shown in FIG. 7, the variable receiving antenna unit 14v that is movable in the vertical direction or the lateral direction is provided in the screening device 4 according to the embodiment. A transmitting/receiving antenna unit 17p that includes the multiple transmitter/receivers 16 and the multiple directional antennas 12a is further provided. The transmitter/receivers 16 and the directional antennas 12a of the transmitting/receiving antenna unit 17p are disposed to be stacked in the vertical direction.

The variable directional antenna 12v is provided to oppose the directional antennas 12a; and the screening subject a is disposed between the directional antennas 12a of the transmitting/receiving antenna unit 17p and the variable directional antenna 12v of the variable receiving antenna unit 14v when the screening subject α is screened.

Effects of the embodiment will now be described.

In the embodiment, the screening of the interior of the screening subject α can be performed by detecting the transmitted wave 21; and the screening of the surface of the screening subject α can be performed by detecting the diffracted wave 22. By using the transmitting/receiving antenna unit 17p, precise screening of the surface of the screening subject α can be performed by detecting the reflected wave 23; and the positional information of the screening subject α can be acquired. Further, by moving the variable receiving antenna unit 14v in the vertical direction or the lateral direction, the screening subject α can be scanned using a beam having a narrow directivity. Thereby, the screening of the screening subject α can be performed by combining scanning using the pulse microwaves 20 while mechanically moving the variable receiving antenna unit 14v and beam scanning using, for example, a phased array that can electronically provide narrow directivity.

According to the embodiment, screening information for a wider area of the screening subject α can be acquired by using the variable receiving antenna unit 14v. The screening of the screening subject α can be performed with higher precision by the reflected wave 23 being received by the multiple directional antennas 12a.

A fifth embodiment will now be described.

Figure 8:
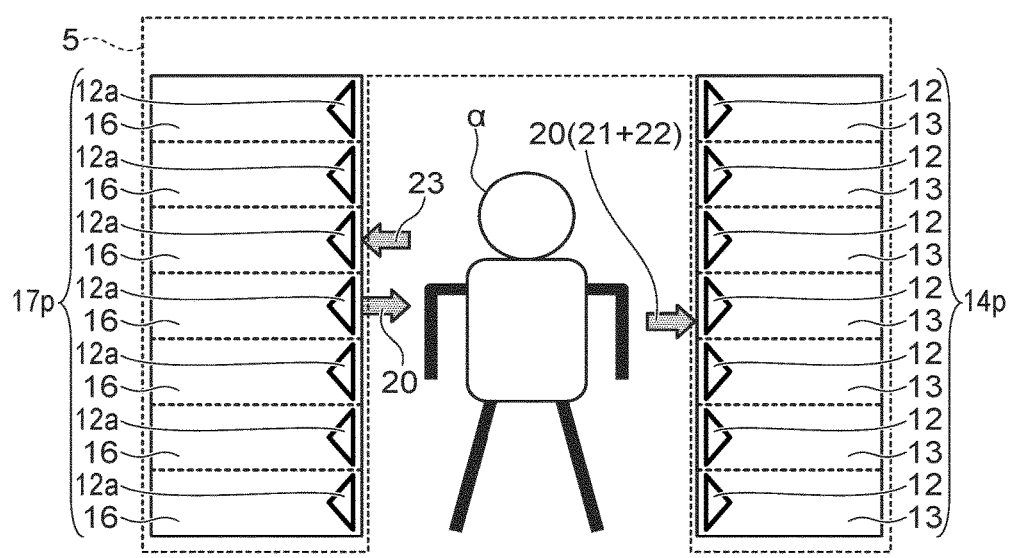
FIG. 8 is a conceptual view showing a screening device according to a fifth embodiment.

FIG. 8 is a conceptual view showing the screening device according to the embodiment.

As shown in FIG. 8, the transmitting/receiving antenna unit 17p is provided in the screening device 5 according to the embodiment. A receiving antenna unit 14p that includes the multiple receivers 13 and the multiple directional antennas 12 is further provided. The receivers 13 and the directional antennas 12 of the receiving antenna unit 14p are disposed to be stacked in the vertical direction.

The multiple directional antennas 12a are provided to oppose the multiple directional antennas 12. The screening subject α is disposed between the directional antennas 12a and the directional antennas 12 when the screening subject α is screened.

Effects of the embodiment will now be described.

In the embodiment, by the multiple receiving antenna units 14p receiving the pulse microwaves 20 transmitted from the multiple transmitting/receiving antenna unit 17p, the screening can be performed for a wider area of the screening subject α without moving the directional antennas 12.

According to the embodiment, the screening of the screening subject α can be performed with higher precision without moving the directional antennas 12 and the receivers 13.

A sixth embodiment will now be described.

Figure 9:
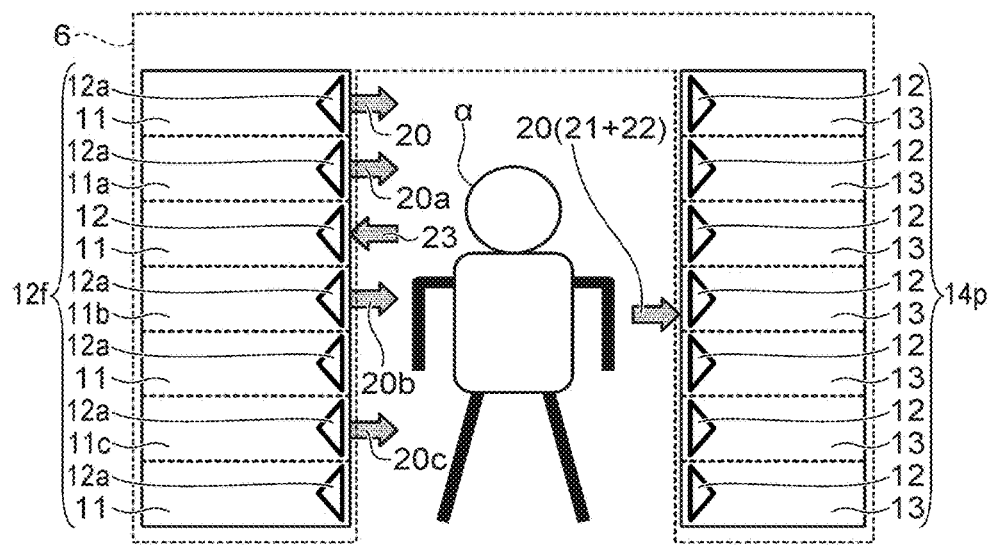
FIG. 9 is a conceptual view showing a screening device according to a sixth embodiment.

FIG. 9 is a conceptual view showing a screening device according to the embodiment.

As shown in FIG. 9, the receiving antenna unit 14p and a transmitting/receiving antenna unit 12f are provided in the screening device 6 according to the embodiment. The transmitting/receiving antenna unit 12f includes multiple transmitters 11, 11a, 11b, and 11c. The transmitters 11a, 11b, and 11c can transmit pulse microwaves 20a, 20b, and 20c of frequencies that are different from that of the transmitter 11. Also, the transmitting/receiving antenna unit 12f includes the multiple directional antennas 12a.

The multiple directional antennas 12a are provided to oppose the directional antennas 12.

Effects of the embodiment will now be described.

In the embodiment, because the frequencies of the pulse microwaves 20, 20a, 20b, and 20c transmitted by the transmitters 11, 11a, 11b, and 11c are different, information for each frequency can be transmitted to the receivers 13. Thereby, the depth in the interior of the screening subject α where an article such as a metal or the like exists can be known.

According to the embodiment, the screening subject α can be screened three-dimensionally without exposing the screening subject α to electromagnetic waves in the short wavelength band which may have negative effects on organisms.

According to the embodiments described above, a screening device that can view the interior of the screening subject α can be realized without exposing the screening subject α to radiation.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A screening device, comprising:
  a first antenna configured to transmit a first microwave to a human body to generate a second microwave and a third microwave, the second microwave being generated by a diffraction of the first microwave at the human body, the third microwave being a part of the first microwave passing through the human body; and
  a second antenna configured to receive the second microwave in a first period and to receive the third microwave in a second period,
  the screening device screening an interior of the human body by detecting the third microwave, and
  the screening device screening a surface of the human body by detecting the second microwave.

2. The device according to claim 1, wherein
  the second antenna does not receive the second microwave in the second period,
  the second antenna does not receive the third microwave in the first period.

3. The device according to claim 1, wherein
  a first antenna includes:
    a transmitter configured to generate the first microwave; and
    a transmitting antenna part connected with the transmitter, the transmitting antenna part being configured to irradiate the first microwave.

4. The device according to claim 1, wherein
  a first antenna includes:
    a movable part; and
    the first antenna is movable in a vertical direction or a lateral direction by movable part.

5. The device according to claim 4, wherein
  the second antenna includes:
    a variable directional antenna part configured to receive the second microwave and the third microwave;
    a receiver connected with the variable directional antenna; and
    the variable directional antenna selectively receives the second microwave and third microwave output from first antenna by changing a receiving direction of the variable directional antenna.

6. The device according to claim 1, further comprising:
  a third antenna configured to transmit a first microwave to a subject from a different angle from the first antenna to generate a second microwave and a third microwave.

7. The device according to claim 6, wherein
  the second antenna includes:
    a variable directional antenna part configured to receive the second microwave and the third microwave;
    a receiver connected with the variable directional antenna; and the variable directional antenna receives the second microwave and third microwave output from first antenna or second antenna selectively by changing a receiving direction of the variable directional antenna.

8. The device according to claim 7, wherein the number of elements of the variable directional antenna is greater than the number of elements of the transmitting antenna.

9. The device according to claim 1, wherein the first microwave includes a pulse microwave.

10. A screening device, comprising:
a first antenna including a transmitter/receiver and a first directional antenna, the transmitter/receiver being configured to transmit a first microwave to a human body to generate a second microwave and a third microwave, the second microwave being generated by a diffraction of the first microwave at the human body, the third microwave being a part of the first microwave passing through the human body, and the transmitter/receiver being configured to receive a reflected first microwave, the first directional antenna being connected with the transmitter/receiver; and
a second antenna including a receiver and a second directional antenna, the receiver being configured to receive the second microwave in a first period and to receive the third microwave in a second period, the second directional antenna being connected with the receiver,
the screening device screening an interior of the human body by detecting the third microwave, and
the screening device screening a surface of the human body by detecting the second microwave.

11. The device according to claim 10, wherein
the receiver does not receive the second microwave in the second period,
the receiver does not receive the third microwave in the first period.

12. The device according to claim 10, wherein
a plurality of the transmitter/receivers and a plurality of the first directional antennas are provided in the first antenna, and
the second directional antenna is a variable directional antenna having a changeable receiving direction.

13. The device according to claim 10, wherein the second directional antenna is movable in a vertical direction or a lateral direction.

14. The device according to claim 10, wherein
a plurality of the transmitter/receivers and a plurality of the first directional antennas are provided in the first antenna, and
a plurality of the receivers and a plurality of the second directional antennas are provided in the second antenna.

15. The device according to claim 10, wherein a frequency of the first microwave transmitted from at least one of the transmitter/receivers of the plurality of the transmitter/receivers is different from a frequency of the first microwave transmitted from one other transmitter/receivers.

16. The device according to claim 10, wherein the first directional antenna includes a superconducting material.

17. The device according to claim 10, wherein the second directional antenna includes a superconducting material.

* * * * *